United States Patent [19]

Currie et al.

[11] Patent Number: 4,960,698
[45] Date of Patent: Oct. 2, 1990

[54] PROCESS FOR PRODUCING L-654,040, ANTIBACTERIAL AGENT

[75] Inventors: Sara A. Currie, Roselle; Thomas W. Miller, Cartoret; Eugene L. Dulaney, Summit; James P. Springer, Mountainside; Mary E. Valiant, Plainfield, all of N.J.; Sagrario M. del Val, Madrid, Spain; Sheldon B. Zimmerman, Springfield, N.J.

[73] Assignee: Merck & Co., Inc., Rahway, N.J.

[21] Appl. No.: 349,279

[22] Filed: May 9, 1989

Related U.S. Application Data

[62] Division of Ser. No. 164,707, Mar. 7, 1988, abandoned.

[51] Int. Cl.$^5$ .................. C12P 17/16; C12P 17/14; C12P 1/06; C12N 1/00
[52] U.S. Cl. .................. 435/119; 435/120; 435/169; 435/908
[58] Field of Search ............... 435/908, 119, 822, 118, 435/169, 120

[56] References Cited

U.S. PATENT DOCUMENTS 4,189,472 2/1980 Hasegawa .................. 435/130

OTHER PUBLICATIONS

"The Biology of Actinomycetes", Goodfellow et al., ed., 1984, pp. 104–105.

*Primary Examiner*—Elizabeth C. Weimar
*Assistant Examiner*—Irene Marx
*Attorney, Agent, or Firm*—Mark R. Daniel; Charles M. Caruso

[57] ABSTRACT

L-654,040 of the structure:

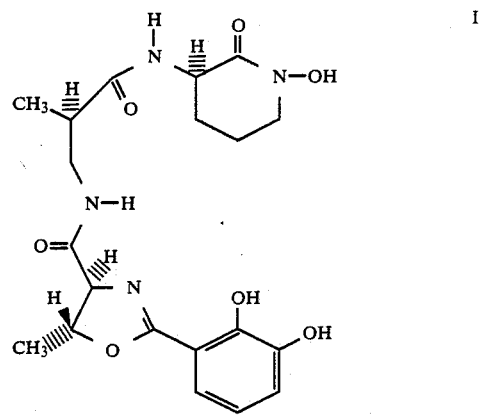

is a novel antibacterial and isolated from the novel organism *Streptoverticillium synroense*, strain MA6011, deposited at the ATCC.

1 Claim, No Drawings

PROCESS FOR PRODUCING L-654,040, ANTIBACTERIAL AGENT

This is a division of application Ser. No. 164,707, filed Mar. 7, 1988, now abandoned.

BACKGROUND OF THE INVENTION

1. Field of the Invention

The present invention relates to a novel antibacterial compound, L-654,040 of Structure I having the formula name: 2-(2,3-dihydroxyphenyl)-4,5-dihydro-N-[3-[(1-hydroxy-2-oxo-3(R)-piperidi -2(R)-methyl-3-oxopropyl]-5R-methyl-4S-oxazolecarboxamide. The present invention encompasses the novel antibacterial in dilute forms, as crude concentrates, in pure forms, and in formulations suitable for antibiotic applications.

The novel compound L-654,040 is useful as an antibacterial agent, showing potency in vitro against numerous microorganisms. When injected intraperitoneally L-654,040 increases survival time of mice infected with *Pasteurella multocida.*

The present invention also relates to a process for preparing the novel antibacterial compound, L-654,040, by fermentation of a nutrient medium with *Streptoverticillium synroense* MA6011, which is a newly discovered species. This strain, MA6011, produces the novel antibacterial compound of the present invention, L-654,040.

The present invention provides a new and useful antibiotic agent with antibacterial activity, as well as a process for preparing the agent by fermentation of a nutrient medium.

SUMMARY OF THE INVENTION

In accordance with the present invention, there is provided an antibacterial compound of the formula:

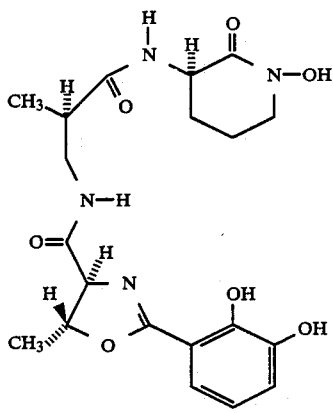

and a pharmaceutically acceptable salt, hydrate, ester, anhydride or amide thereof.

Chart 1: Schematic diagram of steps for isolating L-654,040.

DETAILED DESCRIPTION OF THE INVENTION

Antibacterial L-654,040 is obtained by growing under controlled conditions the microorganism *Streptoverticillium synroense* MA6011, ATCC 53699 in a fermentation broth. The fermentation may be carried out in media containing suspended nutrient matter or in predominantly clear media wherein the medium is substantially free of suspended nutrient matter.

Based on extensive taxonomic studies, the antibiotic producing microorganism is identified as the new species *Streptoverticillium synroense*. A useful strain is designated MA 6011 in the culture collection of MERCK & CO., Inc., Rahway, N.J. On or about Dec. 10, 1987, a culture thereof has been placed on permanent deposit with the culture collection of the American Type Culture Collection, 12301 Parklawn Drive, Rockville, Maryland 20852, and has been assigned Accession No. ATCC 53699.

MORPHOLOGICAL AND CULTURAL CHARACTERISTICS OF STREPTOVERTICILLIUM SYNROENSE MA6011, ATCC 53699

The morphological and cultural characteristics of *Streptoverticillium synroense* MA6011, ATCC 53699 are set forth below.

Morphology:

Using standard media and procedures, morphological and cultural characteristics of the producing organism were examined according to Bergey, *Manual of Determinative Bacteriology*, 8th Edition, Williams & Wilkins. Based on comparison with the published description of other species of the genus *Streptoverticillium*, it was determined that the producing organism is a new strain of a new species, identified in the Merck collection as *Streptoverticillium synroense*, strain MA6011.

CULTURAL CHARACTERISTICS OF STREPTOVERTICILLIUM SYNROENSE MA-6011, PRODUCING ORGANISM OF L-654,040

A. *Morphology*:

Sporophores form short branches produced in a verticil or whorl at intervals along the aerial mycelia. These branches in turn produce several secondary branches that form straight chains of 10–15 spores. Spore surface appears rough, almost warty at high magnifications (EM).

| Yeast Extract-Malt Extract (ISP Medium 2) | |
|---|---|
| $V^1$: | Reverse—black |
| A: | Mixed light and medium gray |
| SP: | Very dark brown |
| Oatmeal Agar (ISP Medium 3) | |
| V: | Reverse—dark brown |
| A: | Light gray with floccose white areas |
| SP: | Dark brown |
| Inorganic Salts-Starch Agar (ISP Medium 4) | |
| V: | Reverse—brown |
| A: | Light gray with areas of floccose white |
| SP: | Slight browning of medium |
| Glycerol Asparagine Agar (ISP Medium 5) | |
| V: | Reverse—dark brown |
| A: | Medium gray edged with dark gray and white mixed |
| SP: | Dark brown |
| Peptone-Iron-Yeast Extract Agar (ISP Medium 6) | |
| V: | Tan |
| A: | None |
| SP: | Dark brown |

| | |
|---|---|
| Melanin: | Positive |
| Tyrosine Agar | |
| (ISP Medium 7) | |
| V: | Reverse—black |
| A: | Gray |
| SP: | Dark brown to black |
| Czapek-Dox Agar | |
| V: | Colorless, moderate |
| A: | Sparse, grayish white |
| SP: | None |

All readings were taken after three weeks at 28° C. unless noted otherwise. The pH of all media was approximately neutral (6.8–7/2).
[1]V = Vegetative Growth; A = Aerial Mycelium; SP = Soluble Pigment B. Carbon Utilization:

| Pridham-Gottlieb Basal Medium (ISP Medium 9) + 1% Carbon Source; | |
|---|---|
| Glucose | + |
| Arabinose | ± |
| Cellulose | − |
| Fructose | + |
| Inositol | ± |
| Lactose | ± |
| Maltose | + |
| Mannitol | + |
| Mannose | + |
| Raffinose | ± |
| Rhamnose | ± |
| Sucrose | + |
| Xylose | + |

+ = Growth; ± = Growth Poor or Questionable;
− = No Growth as Compared to Negative Control (No Carbon Source)

C. Temperature Range
(Yeast Extract-Dextrose +Salts Agar)
28° C. - Good vegetative and aerial growth with sporulation
37° C. - Good vegetative and aerial growth with sporulation
42° C. - Good vegetative growth, sparse aerial with poor sporulation
50° C. - No growth D. Oxygen Requirements
(Stab Culture in Yeast Extract-Dextrose +Salts Agar):. Aerobic, grows on top.

PREPARATION OF L-654,040

The novel antibacterial compound of the present invention is produced during the aerobic fermentation of suitable aqueous nutrient media under controlled conditions via inoculation with the organism *Streptoverticillium synroense*. Aqueous media, such as those employed for the production of other antibiotics are suitable for producing the novel antibacterial compound of the present invention. Such media contain sources of carbon, nitrogen and inorganic salts assimilable by the microorganism. Many fermentation media support production of L-654,040 by *Streptoverticillium synroense* MA6011, ATCC 53699, and may be suitably adjusted within the ordinary skill of the fermentation microbiologist.

In general, carbohydrates, for example, glucose, fructose or starches as well as glycerol, pectin or peptonized milk either alone or in combination can be used as sources of assimilable carbon in the nutrient medium. The exact quantity of the carbon source or sources utilized in the medium depends in part upon the other ingredients of the medium but, in general, the amount of carbon source usually varies between about 1% and 6% by weight of the medium. These carbon sources can be used individually or several such carbon sources can be combined in the medium.

Many proteinaceous materials may be used as nitrogen sources in the fermentation process. Suitable nitrogen sources include, for example, yeast extract, yeast hydrolysates, soybean flour, distillers solubles, corn steep, peptonized milk, lard water, peanut meal and tomato paste and the like. The sources of nitrogen, either alone or in combination, are used in amounts ranging from about 0.2% to 6% by weight of the aqueous medium.

Among the nutrient inorganic salts which may be incorporated in the medium are the customary salts capable of yielding sodium, potassium, ammonium, calcium, magnesium, phosphate, sulfate, chloride, carbonate and the like ions. Also, there may be included trace metals such as cobalt, manganese and iron.

The fermentation is carried out at temperatures ranging from about 20° C. to about 42° C. The pH of the nutrient media suitable for growing *Streptoverticillium synroense* MA6011, ATCC 53699 culture and producing the novel antibacterial compound of the present invention should be in the range of from about 5.5 to 8.0.

Small scale fermentation of the antibiotic conveniently is carried out by inoculating a suitable nutrient medium with the antibiotic-producing culture and, after transfer to a production medium, permitting fermentation to proceed at a constant temperature on a shaker for several days. At the end of the incubation period, the antibiotic activity is isolated from the fermentation broth by techniques hereinafter described.

The small scale fermentation may be conducted in a sterilized flask via a one, two, three or four-stage seed development. The nutrient medium for the seed stage may be any suitable combination of carbon and nitrogen sources. The seed flask is shaken in a constant temperature chamber until maximum growth is completed (usually 1–3 days) and some of the resulting growth is used to inoculate either a further seed-stage or the production medium. Intermediate stage seed-flasks, when used, are developed essentially in the same manner; that is, part of the contents of the flask is used to inoculate either the next stage seed medium or the production medium. The inoculated production flasks are shaken at a constant temperature for several days (usually 3 to 5 days) and at the end of the incubation period the novel antibacterial compound of the present invention is isolated.

For large scale work, it is preferable to conduct the fermentation in suitable tanks provided with an agitator and a means of aerating the fermentation medium. The nutrient medium is made up in the tank and sterilized by heating to about 120° C. Upon cooling, the sterilized medium is inoculated with a previously grown seed culture of the producing organism and fermentation is permitted to proceed for a period of several days (3 to 5 days, for example) while agitating and/or aerating the nutrient medium and maintaining a constant temperature.

It will be understood that, given the guidelines and experimental protocols of this application, the determination of appropriate fermenting or culturing conditions for *Streptoverticillium synroense*, particularly strain MA6011 ATCC 53699, is well within the scope of this invention. Such conditions, including small and large scale fermentation of *Streptoverticillium*, are conventional adaptations or common variations easily ascertained by one with the requisite skills.

When used as an antibacterial, L-654,040 may be employed in the form of pharmaceutical preparations which contain it in admixture or conjunction with an organic or inorganic solid or liquid pharmaceutical excipient suitable for internal, parenteral or local administration. Suitable excipients are substances that do not react with the antibiotic, for example, water, gelatin, lactose, starches, stearyl alcohol, magnesium stearate, talcum, vegetable oils, benzyl alcohols, gums, propylene glycols, polyalkylene glycols, white petroleum jelly, or other known pharmaceutical excipients. The pharmaceutical formulations may be, for example, tablets, ointments, creams or capsules, or in liquid form solutions, suspensions or emulsions. They may be sterilized and/or contain assistants such as preserving, stabilizing, wetting or emulsifying agents, solution promoters, salts for regulating osmotic pressure or buffers.

When it is desired to administer the antibiotic in dry, solid unit dosage form, capsules, boluses or tablets containing the desired amount of antibiotic are employed. These dosage forms are prepared by intimately and uniformly mixing the active ingredient with suitable finely divided diluents, fillers, disintegrating agents and/or binders such as, for example, starch, lactose, talc, magnesium stearate, vegetable gums and the like. Such unit dosage formulations may be varied widely with respect to their total weight and content of antibacterial L-654,040 depending upon factors such as the type of host to be treated, the severity and type of infection to be treated and the weight of the host. Conveniently, the antibiotic may be administered on a daily basis at from about 5 to about 100 mg per kilogram of body weight.

Included within the scope of the present invention are the non-toxic, pharmaceutically acceptable salts of L-654,040. Such salts include, for example, the alkali metal and alkaline earth metal salts such as those derived from sodium, potassium or calcium or salts derived from ammonium, or salts derived from organic bases such as triethylamine, N-ethylpiperidine, dibenzylethylenediamine and the like.

Also included within the scope of the present invention are the non-toxic, pharmaceutically acceptable esters and amides of L-654,040. Such esters and amides are those which would readily occur to the skilled artisan, and include, for example, $C_{1-4}$ alkyl esters and amides.

EXAMPLE 1

Fermentation of MA6011

A lyophile of MA6011 deposited in the Merck Culture Collection was asceptically transferred to a 250 ml baffled Erlenmeyer flask containing 50 ml of Medium 1 [1.0 g/l dextrose, 10 g/l soluble starch, 3.0 g/l beef extract, 5.0 g/l yeast autolysate (ARDAMINE pH, Yeast Products, Inc.), 5.0 g/l casein enzymatic hydrolysate (NZ AMINE TYPE E, Sheffield), 0.05 g/l $MgSO_4.7H_2O$, ml phosphate buffer (91.0 g $KH_2PO_4$ and 95.0 g $NaHPO_4$ in 1000.0 ml deionized $H_2O$), 0.5 g/l $CaCO_3$, and 1000.0 ml distilled $H_2O$ with presterile pH of 7.0–7.2 adjusted with NaOH], previously sterilized at 121° C. and 16 psi for 20 minutes, and loosely stoppered with a cotton plug. The inoculated flask was shaken at 220 rpm at 28° on a reciprocating shaker for 48 hours. Ten mls of the resulting growth was transferred to a 2-liter baffled Erlenmeyer flask containing 500 mls of Medium 1, sterilized in the same manner above. The flask was shaken at 160 rpm at 28° on the reciprocating shaker for 24 hours.

The entire contents of the second stage inoculum was asceptically transferred to 9.5 liters of Medium 2 (10.0 g/l peanut meal, 15.0 g/l oat flour, 0 5 g/l Na ascorbate, 1.0 g/l Na citrate, 0.5 g/l $K_2HPO_4$, 0.010 g/l $CoCl_2.6H_2O$, 5.0 ml/l Soya Oil, and 1000.0 ml distilled $H_2O$ with presterile pH cf 7.3–7.5 adjusted with NaOH) in a 14-liter stirred jar fermentor. The medium had been sterilized for 20 min at 121° C. and 16 psi in a sterilizer and asceptically transferred to the fermentor which had been previously sterilized for 90 min at 121° C. and 16 psi. The fermentation is allowed to continue with agitation of 400 rpm and aeration of 3 liters/min at 28° C. for a period of 3 to 5 days. Samples of the fermentation broth were removed at 24 hour intervals and assayed for purity, pH, packed cell volume and antibiotic production.

EXAMPLE 2

Isolation of L-654,040

The whole broth from a 14-liter fermentor batch (6.7 liters) was mixed with diatomaceous earth and filtered through a pad of wet diatomaceous earth. The filtrate, 7 liters, containing about 1.4 g of antibiotic, was adjusted to pH 5 and adsorbed on 500 ml of AMBERLITE XAD-2 resin at 35 ml/minute. The adsorbate was washed with water and eluted with 1 liter of $Me_2CO$-$H_2O$ (3:2). The eluate was concentrated under reduced pressure to 200 ml and neutralized with dilute NaOH. The concentrate was extracted with 200 ml of n-butanol (n-BuOH). The extract was washed with 200 ml of $H_2O$ and concentrated to a heavy syrup. Concentrates from two batches were diluted with MeOH to 40 ml and chromatographed on a 1640 ml column of SEPHADEX LH-20 packed in MeOH. The column was developed with MeOH at 15 ml/minute and after a void cut of 500 ml, fractions of 20 ml each were collected. Bioassays indicated the activity was eluted at 0.77 column volumes. Fractions 31–45 were pooled, concentrated to about 40 ml and refrigerated overnight to allow crystallization. The product was filtered, washed with MeOH and dried in vacuum 3 hours. The yield was 527 mg, a 20% recovery from broth. More product was isolated by chromatography of the mother liquors on LH-20 again followed by crystallization. The antibiotic was recrystallized from $H_20$ by heating and cooling. The solubility in boiling water is about 10 mg/ml.

EXAMPLE 3

Physicochemical characterization of L-654,040

1. Elemental analysis called for $C_{20}H_{26}N_4O_7 \cdot H_2O$ :

Calc'd: C, 53.09; H, 6.24; N, 12.38
Found: C, 53.63; H, 6.05; N, 12.46

2. A $^{13}C$ NMR spectrum was recorded in ca 10% $CD_3OD/CDCl_3$ at room temperature on a Varian SC -300 NMR spectrometer. Chemical shifts are given in ppm downfield of internal tetramethylsilane (TMS) at zero ppm. In agreement with the molecular formula $C_{20}H_{26}N_4O_7$, 20 carbons were observed with the following chemical shifts: 15.1, 20.8, 21.5, 27.5, 40.9, 42.9, 50.2, 50.8, 74.6, 79.7, 110.7, 119 5, 119.6, 119.7, 146.2.

148.9, 166.9. 168.3, 173.0, 177.4 ppm. 3. The ultraviolet data showed:

UV λMeOH nm ($E^{1\%}_{1cm}$) 255 (338), 318 (78) max
UV λH$_2$O nm ($E^{1\%}_{1cm}$) 255 (303), 315 (68) max
UV λ0.01N HCl $_{nm}$ ($E^{1\%}_{1cm}$) 267 (390), 340 (65) max
UV λ0.01N NaOH $_{nm}$ ($E^{1\%}_{1cm}$) 255 (sh 290), 335 (75) max 4. X-Ray Crystallography A sample of L-654,040 (Lot L-681,506-12M) was found to form crystals in water. One molecule of water co-crystallizes in the crystal lattice. By X-ray diffraction analysis, the relative configuration was determined, as shown below.

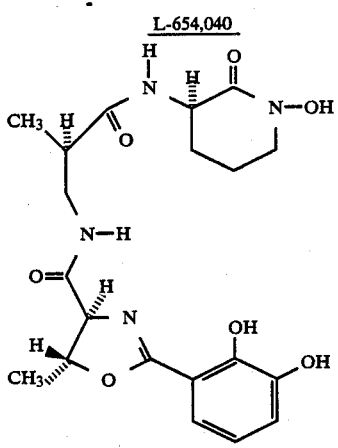

L-654,040                               I

The biosynthetic subunits that make up the molecule, appear to be ornithine, β-aminoisobutyric acid, threonine, and o-pyrocatechuric acid. The structure Of L-654,040 was solved by the application of direct methods. [Main, P. MULTAN, a program for the automatic solution of crystal structures from X-ray diffraction data by multiple starting point tangent formula. University of York, England, 1980.] NMR confirmed structure I.

EXAMPLE 4

Antibiotic Activity

Activity against a variety of microorganisms in culture was demonstrated. A crystalline sample of L-654,040 was dissolved in distilled water. Aliquots of 15λ were deposited on the surface of each seeded nutrient agar susceptibility test plate, followed by overnight incubation. Plates were then measured for activity by determining the inhibition zone diameter under the previously placed 15λ aliquot. The results are presented in Table I.

TABLE I

| Microorganism Merck # | Inhibition Zone Diameter (mm) | |
|---|---|---|
| | 2 mg/ml[b] | 0.5 mg/ml[b] |
| Bacillus sp. 633 | 28 | 23 |
| Proteus vulgaris 1012 | 34 | 24 |
| Pseudomonas aeruginosa 979 | 0 | 0 |
| Staphylococcus aureus 108 (6538P)[a] | 18 | 0 |
| Bacillus subtilis 964 (6633) | 14 | 12 |
| Sarcina lutea 1101 (934) | 17 | 12 |
| Brucella bronchiseptica 965 | 24 | 16 |
| Salmonella gallinarum 1287 | 0 | 0 |
| Vibrio percolans 1272 (8461) | 25 | 18 |
| Xanthomonas vesicatoria 815 | 0 | 0 |
| Proteus vulgaris 838 (21100) | 31 | 18 |
| Escherichia coli 1418 | 13 | 0 |

TABLE I-continued

| Microorganism Merck # | Inhibition Zone Diameter (mm) | |
|---|---|---|
| | 2 mg/ml[b] | 0.5 mg/ml[b] |
| Pseudomonas stutzeri 1231 (11607) | 13 | 12 |
| Klebsiella pneumoniae 1264 | 0 | 0 |
| Aerobacter aerogenes 835 | 0 | 0 |
| Erwinia atroseptica 1159 (4446) | 0 | 0 |
| Pseudomonas aeruginosa 2824 | 0 | 0 |
| Corynebacterium pseudodiph. 261 (9742) | 33 | 28 |
| Escherichia coli 60 (9637) | 0 | 0 |
| Streptococcus faecium 2820 | 0 | 0 |
| Streptococcus agalactiae 2875 | 13 | 12 |
| Proteus vulgaris 2112 (episome) | 28 | 16 |
| Proteus mirabilis 3126 | 25 | 24 |
| Candida albicans 992 | 24 | 16 |
| Aspergillus niger 442 | 0 | 0 |

[a]Numbers in Parentheses = ATCC #
[b]Concentration of L-654,040 in distilled H$_2$O before deposition on the test plate surface.

EXAMPLE 5

Effect of Acetylation

Compound L-654-040 and its acetyl derivative (acetyl-L-654,040) were assayed for capacity to inhibit the growth of numerous additional microorganisms. The compounds L-654,040 and acetyl-L-654,040 were stored at −20° C. They were tested by the agar dilution method using a defined agar medium (antagonist-free medium: Roche formula). L 654,040 was dissolved in water at a concentration of 2.56 mg/ml, by heating in a boiling water bath. Acetyl-L-654,040 was dissolved in methanol and diluted with water to a concentration of 2.56 mg/ml in 30% methanol. Subsequent serial two-fold dilutions of L-654,040 and the acetyl derivative were made with water. D-cycloserine, the control compound for this assay, was dissolved in and diluted with water.

Drug-agar plates were prepared by pouring into each plate mixtures of nine parts of molten agar medium added to one part of diluted antibiotic. A control plate containing a final concentration of 3% methanol also was prepared.

The drug-agar plates for testing by the agar dilution method were inoculated with the test cultures which had just been diluted with antagonist free broth. The final inocula were ca 10$^4$ cfu/spot. After incubation at 35° C. for 20 hours, the plates were examined for growth, and the minimum inhibitory concentration (MIC) was recorded as the lowest concentration of each compound showing no growth no growth or 5 or fewer discrete colonies.

The activity obtained with the parent compound (L-654,040, Lot 654,040-O0lR001), acetylL-654-040 (Lot L-654,506-014S) and the D-cycloserine control are presented in Table II.

TABLE II

| Test Culture | Merck Number | MIC (μg/ml)[a] | | |
|---|---|---|---|---|
| | | L-654-040 | Acetyl-L-654,040 | D-Cycloserine Control |
| Staph. aureus | 2865 | 32.0 | 8.0 | 2.0 |
| Strep. faecalis | 2864 | >256.0 | >256.0 | 4.0 |
| E. coli TEM 2+ | 4351 | >256.0 | >256.0 | 2.0 |
| E. coli DC2 | 4353 | 32.0 | 32.0 | 8.0 |
| E. coli | 2891 | >256.0 | >256.0 | 4.0 |
| Sal. typhimurium | 3860 | >256.0 | >256.0 | 4.0 |
| Ent. cloacae P99− | 2647 | >256.0 | >256.0 | 4.0 |
| Prot. vulgaris | 2829 | >256.0 | >256.0 | 32.0 |

TABLE II-continued

| Test Culture | Merck Number | MIC (μg/ml)[a] | | |
|---|---|---|---|---|
| | | L-654-040 | Acetyl-L-654,040 | D-Cycloserine Control |
| Ps. aeruginosa | 4279 | >256.0 | >256.0 | 16.0 |
| Ser. marcescens | 2840 | >256.0 | >256.0 | >256.0 |

[a]Agar dilution assay; multipoint inoculator; inoculum $10^4$ cfu/spot; antagonist-free medium (Roche); incubation at 35° C. for 20 hours.

The results show that only two strains were sensitive to the parent compound and the acetyl derivative, i.e., Staphylococcus aureus 2865 and one of three strains of Escherichia coli, a permeability mutant. The acetyl derivative was fourfold more active against S. aureus and both had equal activity against the mutant.

EXAMPLE 6

Biological Activity of L-654,040

The agar dilution method of Example 4 was performed in another experiment on a different set of microorganisms, except the procedure in the present experiment substituted the antagonist-free medium (Roche) with trypticase soy agar (BBL). The results are presented in Table III.

TABLE III

In Vitro Activity of Antibiotic L-654,040 and Cefoxitin Against Aerobic Bacteria

| Microorganism | Merck Number | MIC (mcg/ml*) | |
|---|---|---|---|
| | | L-654,040 | CEFOXITIN (Merck) |
| S. aureus Gm[r] Meth[r] | 4310 | 128.0 | >128.0 |
| S. aureus | 2868 | 128.0 | 4.0 |
| S. aureus | 2865 | 64.0 | 2.0 |
| Strep. faecalis | 2864 | >128.0 | >128.0 |
| E. coli TEM 2+ | 4351 | >128.0 | 4.0 |
| E. coli TEM 2+ DC2 | 4352 | 128.0 | 2.0 |
| E. coli DC2 | 4353 | 128.0 | 2.0 |
| E. coli | 2891 | >128.0 | 64.0 |
| Sal. typhimurium | 3860 | >128.0 | 4.0 |
| Ent. cloacae P99+ | 2646 | >128.0 | 128.0 |
| Ent. cloacae P99− | 2647 | >128.0 | 8.0 |
| Ent. aerogenes | 2828 | >128.0 | >128.0 |
| K. pneumoniae K1+ | 4354 | >128.0 | 4.0 |
| K. pneumoniae | 4005 | >128.0 | 2.0 |
| Prot. vulgaris | 2829 | >128.0 | 4.0 |
| Prot. morganii Sm[r] | 2833 | >128.0 | 8.0 |
| Prot. mirabilis Gm[r] | 2830 | >128.0 | 4.0 |
| Ps. aeruginosa RPL11+ | 3350 | >128.0 | >128.0 |
| Ps. aeruginosa | 2835 | >128.0 | >128.0 |
| Ps. aeruginosa | 4279 | >128.0 | >128.0 |
| Ser. marcescens | 2840 | >128.0 | 32.0 |

*Agar dilution assay; multipoint inoculator; inoculum $10^4$ cfu/spot; trypticase say agar (BBL) incubation at 35° C. for 20 hours.

EXAMPLE 7

Biological Activity of L-654,040

The agar dilution method of Example 4 was performed in another experiment on a different set of microorganisms, except that (a) Wilkens-Chalgren agar was used instead of antagonist-free medium (Roche);

(b) The inoculum/spot was about $10^6$ instead of about $10^4$;

(c) The incubation period was for 48 hours, not 24 hours; and (d) Incubations were performed under anaerobic conditions.

The results are presented in Table IV.

TABLE IV

In Vitro Activity of Antibiotic L-654,040 and Cefoxitin Against Anaerobic Bacteria

| Organism | Merck Number | MIC (mcg/ml)* | |
|---|---|---|---|
| | | L-654,040 | CEFOXITIN (Merck) |
| Actinomyces naeslundii | 4053 | 128.0 | 0.015 |
| Eubcterium limosum | 3344 | 128.0 | 1.0 |
| Propionibacterium acnes | 2249 | 128.0 | 0.06 |
| Peptostreptococcus anaerobius | 3282 | >128.0 | 1.0 |
| Clostridium perfringens NCCLS control strain | 4418 | 64.0 | 1.0 |
| C. perfringens | 2237 | 128.0 | 2.0 |
| C. perfringens | 3508 | 64.0 | 0.25 |
| C. perfringens | 3509 | 64.0 | 0.25 |
| C. perfringens | 3510 | 128.0 | 0.5 |
| C. perfringens | 3511 | 64.0 | 1.0 |
| C. perfringens | 3512 | 64.0 | 1.0 |
| C. perfringens | 3513 | 128.0 | 2.0 |
| C. ramosum | 4272 | 64.0 | 32.0 |
| C. difficile Clind[r] | 4273 | 128.0 | 4.0 |
| C. difficile Fox[r] | 4380 | 128.0 | 64.0 |
| Bifidobacterium dentium Fox[r] | 4427 | >128.0 | 64.0 |
| Bacteroides fragilis Met[r], Pen[r] | 4324 | 128.0 | 4.0 |
| B. fragilis Pen[r] | 3214 | >128.0 | 16.0 |
| B. fragilis Clind[r], Fox[r], Tet[r] | 4360 | >128.0 | 32.0 |
| B. fragilis NCCLS control strain | 4419 | >128.0 | 8.0 |
| B. distasonis Pen[r], Fox[r], Clind[r] | 4361 | >128.0 | 32.00 |
| B. distasonis Pen[r], Fox[r] | 3445 | >128.0 | 128.0 |
| B. ovatus Pen[r] | 3248 | >128.0 | 32.0 |
| B. thetalotamicron Clind[r] | 4362 | >128.0 | 32.0 |
| B. thetalotamicron Clind[r], NCCLS control strain | 4420 | >128.0 | 32.0 |
| B. asaccharolyticus | 4271 | >128.0 | 0.5 |
| Fusobacterium mortiferum Fox[r] | 3345 | >128.0 | 32.0 |
| Veillonella alcalescens | 1952 | >128.0 | 1.0 |

*Agar dilution assay, multipoint inoculator, Wilkens-Chalgren agar, inoculum $10^6$ cfu/spot, incubation at 35° C. for 48 hours.

EXAMPLE 8

In Vivo Efficacy in Mice

Protection and survival time against infection, as well as combined therapy with erythromycin, were examined to the extent of finding efficacy in vivo.

Female Charles River CDI mice were infected with Pasteurella multocida (4678) or Bordetella bronchiseptica (3771) by intraperitoneal injection of broth culture dilutions. Erythromycin and/or L-654,040 were then administered intraperitoneally 0 and 6 hours afterwards. Both antibiotics were administered as solutions in water, but prior heating of L-654,040 in a boiling water bath was necessary for solubility. In the combined therapy test, both erythromycin and L-654,040 were titrated alone or erythromycin was titrated in the presence of two fixed levels of L 654,040.

All antibiotics were administered as two separate doses at different abdominal sites. Each erythromycin titration consisted of at least four dosage levels in fourfold increments, and there were five mice at each level.

The mice were observed for 7 days at which time the median effective dose ($ED_{50}$) or median lethal dose of the culture ($LD_{50}$) were calculated by the method of Knudsen, L.F. et al., J. Amer. Stat. Assoc. 42, 282 (1947).

Due to limited solubility and availability, the highest levels of L-654,040 tested were 160 mg/kg ×2 intraperitoneal doses, a level also shown by previous experiments to be tolerated by uninfected mice. At this level, prolongation of survival time was observed after either *Bondetella* or *Pasteurella* infection, but the prolongation of survival was statistically significant (0.025 <p <0.05) only in the Pasteurella -infected animals.

Other experiments showed that when L-654,040 was combined with erythromycin for treatment of a Pasteurella infection, the combined therapy was slightly more effective than erythromycin alone but not to a degree considered to be synergistic.

In summary. L-654,040. when administered intraperitoneally, did not protect but did prolong the survival time of mice infected with *Pasteurella multocida* or *Bordetella bronchiseptica*. This prolonged survival was statistically significant at one level in two *Pasteurella* tests.

While the foregoing specification teaches the principles of the present invention, with examples for the purpose of illustration, it will be understood that the practice of the invention encompasses all of the usual variations, adaptions, modification, deletions or additions of procedures and protocols described herein, as come within the scope of the following claims and its equivalents.

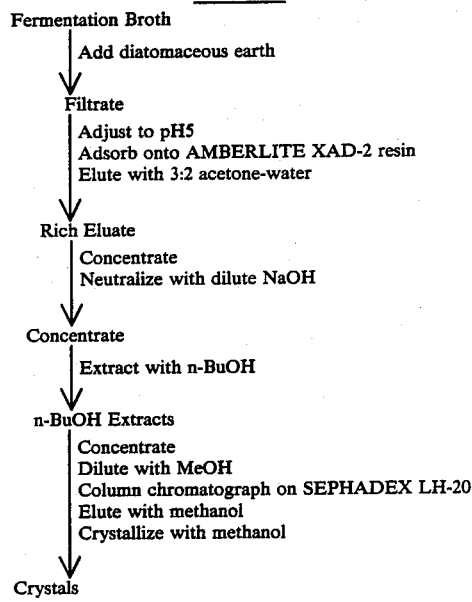

What is claimed is:

1. A method of preparing a compound of Formula I which comprises aerobically cultivating *Streptoverticillium synroense* strain MA6011, ATCC 53699, in an aqueous nutrient medium containing assimilable sources of carbon, nitrogen and inorganic salts under submerged aerobic conditions and recovering said compound.